(12) United States Patent
Adams et al.

(10) Patent No.: US 11,154,558 B2
(45) Date of Patent: Oct. 26, 2021

(54) PREVENTION OF ATHEROSCLEROTIC EVENTS WITH DIRECT FACTOR XA INHIBITORS

(71) Applicant: Adams Pharmaceuticals LLC, New York, NY (US)

(72) Inventors: Jonathan Adams, New York, NY (US); Peter Jeffrey Adams, New York, NY (US)

(73) Assignee: Adams Pharmaceuticals LLC, New York, NY (US)

( * ) Notice: Subject to any disclaimer, the term of this patent is extended or adjusted under 35 U.S.C. 154(b) by 0 days.

(21) Appl. No.: 15/482,073

(22) Filed: Apr. 7, 2017

(65) Prior Publication Data
US 2017/0296549 A1    Oct. 19, 2017

Related U.S. Application Data

(60) Provisional application No. 62/322,891, filed on Apr. 15, 2016.

(51) Int. Cl.

| | |
|---|---|
| *A61K 31/5377* | (2006.01) |
| *A61K 31/437* | (2006.01) |
| *A61K 31/4427* | (2006.01) |
| *A61K 31/4365* | (2006.01) |
| *A61K 31/4425* | (2006.01) |
| *A61K 9/20* | (2006.01) |
| *A61K 31/44* | (2006.01) |
| *A61K 31/444* | (2006.01) |
| *A61K 31/4545* | (2006.01) |

(52) U.S. Cl.
CPC ............ *A61K 31/5377* (2013.01); *A61K 9/20* (2013.01); *A61K 31/437* (2013.01); *A61K 31/4365* (2013.01); *A61K 31/44* (2013.01); *A61K 31/444* (2013.01); *A61K 31/4425* (2013.01); *A61K 31/4427* (2013.01); *A61K 31/4545* (2013.01)

(58) Field of Classification Search
CPC .............. A61K 31/5377; A61K 31/437; A61K 31/4427; A61K 31/4425; A61K 31/4365
USPC ...................................... 514/236.8
See application file for complete search history.

(56) References Cited

U.S. PATENT DOCUMENTS

| | | | |
|---|---|---|---|
| 5,385,885 A | 1/1995 | Gasic et al. | |
| 6,555,542 B1 * | 4/2003 | O'Connor | C07D 211/56 514/183 |
| 2012/0087978 A1 * | 4/2012 | Nause | A61K 9/0004 424/465 |

FOREIGN PATENT DOCUMENTS

| | | | |
|---|---|---|---|
| WO | 2010/147978 A1 | 12/2010 | |
| WO | WO-2013151719 A2 * | 10/2013 | ............ C07D 413/14 |

OTHER PUBLICATIONS

Esmon, Charles, Thrombosis and Haemostasis (2013), vol. 111, pp. 625-633.*
Kalz et al, J. Throm Thrombolysis (2014), vol. 37, pp. 45-55.*
Zhou et al, Mediators of Inflammation, vol. 2011, pp. 1-10.*
(Continued)

*Primary Examiner* — Craig D Ricci
*Assistant Examiner* — Janet L Coppins
(74) *Attorney, Agent, or Firm* — Maier & Maier, PLLC

(57) ABSTRACT

The use of direct factor Xa inhibitors, administered in a dose sufficient to reduce the activity of factor Xa to about 25% less than normal or lower, has the effect of preventing the onset of atherosclerosis, and stabilizing atherosclerotic lesions, and preventing the occurrence or recurrence of atherosclerotic events.

13 Claims, 1 Drawing Sheet

(56) References Cited

OTHER PUBLICATIONS

Eriksson et al, Annu Rev Med 2011, vol. 62, pp. 41-57. (Year: 2011).*
Bansilal et al, American Heart Journal (Oct. 2015), vol. 170(4), pp. 675-682.e8. (Year: 2015).*
Paccaly et al, J Clin Pharmacology 2006, vol. 46, pp. 37-44. (Year: 2006).*
Martinez et al, Am J Health Syst Pharm (2011), vol. 68(18), pp. 1716-1722. (Year: 2011).*
NIH, U.S. National Library of Medicine, ClinicalTrials.gov: https://clinicaltrials.gov/ct2/show/NCT02376010, pp. 1-5. (Year: 2015).*
Internet Archive Wayback Machine, webpage showing first access of ClinicalTrials.gov article on Oct. 2, 2015. (Year: 2015).*
Kubitza et al "Safety, pharmacodynamics, and pharmacokinetics of BAY 59-7939—an oral, direct Factor Xa inhibitor—after multiple dosing in healthy male subjects." Eur J Clin Pharmacol (2005) 61: 873-880. (Year: 2005).*
NIH, U.S. National Library of Medicine, ClinicalTrials.gov: https://clinicaltrials.gov/ct2/show/NCT02090075, pp. 1-8. (Year: 2015).*
Internet Archive Wayback Machine, webpage showing first access of https://clinicaltrials.gov/ct2/show/NCT02090075, on Sep. 27, 2015, pp. 1-2. (Year: 2015).*
Transmittal of the International Search Report and the Written Opinion of the International Searching Authority dated Jul. 11, 2017, in connection with corresponding international application No. PCT/US2017/027099 filed Apr. 12, 2017 (5 pgs.).
Japanese Office Action dated Sep. 10, 2019, in connection with corresponding JP Application No. 2019-505125 (12 pgs., including machine-generated English translation).
Tomoya Hara, "Suggestion of Possibility of Rivaloxaban to Contribute to Suppression of Progress of Arteriosclerotic Lesions by Suppressing Inflammatory Reactions", in Therapeutic Research, 2014, vol. 35, No. 1, pp. 32-34 (4 pgs.).
Tomoya Hara, "Rivaroxaban, a novel oral anticoagulant, attenuates atherosclerotic plaque progression and destabilization in ApoE-deficient mice", in Atherosclerosis, 2015, vol. 242, No. 2, pp. 639-646 (9 pgs.).
Maryna Bondarenko, et al., "Efficacy and Toxicity of Factor Xa Inhibitors", in Journal of Pharmaceutical Science, 2013, vol. 16, No. 1, pp. 74-88 (16 pgs.).
Canadian Office Action dated Nov. 20, 2019, in connection with corresponding CA Application No. 3,020,751 (4 pgs.).
Search Report dated Mar. 12, 2020 in corresponding European Application No. 17783020.5; 8 pages.
Spronk et al., "Pleiotropic effects of factor Xa and thrombin: what to expect from novel anticoagulants", Cardiovascular Research, vol. 101, No. 3, Jan. 2, 2014, pp. 344-351.
Namba et al., "Effects on bone metabolism markers and arterial stiffness by switching to rivaroxaban from warfarin in patients with atrial fibrillation", Heart Vessels, vol. 32, No. 8, Feb. 23, 2017, pp. 977-982.
Mannucci et al., "Recessively inherited coagulation disorders", Blood, vol. 104, No. 5, Sep. 1, 2004, pp. 1243-1252.
Machin et al., "Factor X deficiency in the neonatal period", Arch Dis Child, May 1980; vol. 55, No. 5, pp. 406-408.
Peyvandi et al., "Treatment of rare factor deficiencies in 2016", Treatment of Congenital Bleeding Disorders, American Society of Hematology, Dec. 2, 2016, pp. 663-669.
Peyvandi et al., "Coagulation factor activity and clinical bleeding severity in rare bleeding disorders: results from the European Network of Rare Bleeding Disorders", Journal of Thrombosis and Haemostasis, vol. 10, Feb. 9, 2012, pp. 615-621.
Girolami et al., "Congenital factor X deficiencies with a defect only or predominantly in the extrinsic or in the intrinsic system: A critical evaluation", American Journal of Hematology, 2008, pp. 667-671.
Wool et al., "Pathology Consultation on Anticoagulation Monitoring", American Society for Clinical Pathology, Oct. 4, 2013, pp. 623-634.
Office Action dated Feb. 18, 2020 in corresponding Korean Application No. 10-2018-7032963; 10 pages including English-language translation.
Hara et al., "Rivaroxaban, a novel oral anticoagulant, attenuates atherosclerotic plaque progression and destabilization in ApoE-deficient mice", Atherosclerosis, 2015, vol. 242, pp. 639-646.
Bondarenko et al., "Efficacy and Toxicity of Factor Xa Inhibitors", J. Pharm Pharmaceut Sci., 2013, vol. 16, No. 1, pp. 74-88.

* cited by examiner

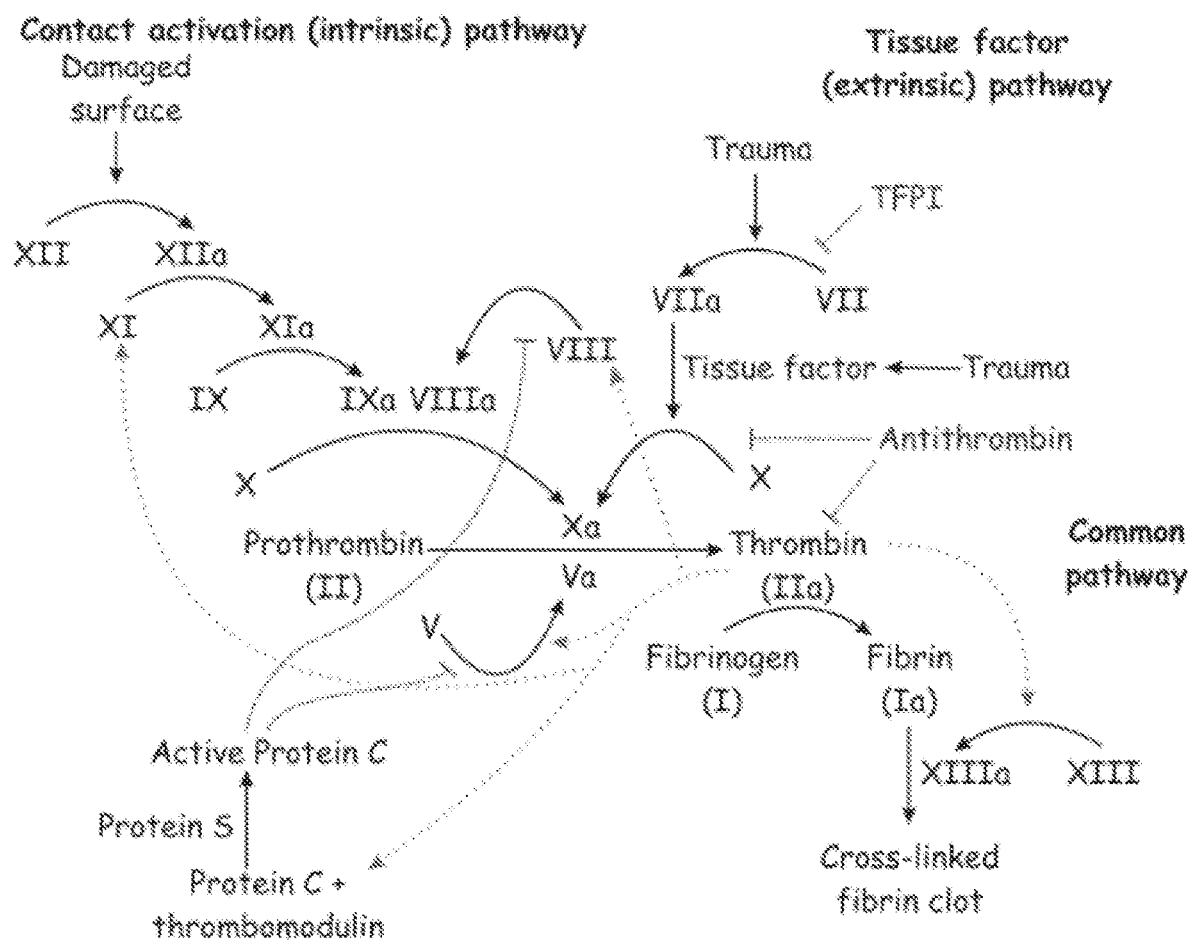

PREVENTION OF ATHEROSCLEROTIC EVENTS WITH DIRECT FACTOR XA INHIBITORS

PRIORITY

This invention claims priority to U.S. Patent Application Ser. No. 62/322,891, entitled "Prevention of Atherosclerotic Events With Direct Factor Xa Inhibitors," filed on Apr. 15, 2016, the contents of which are hereby incorporated by reference in their entirety.

FIELD OF THE INVENTION

This invention relates to the use of direct factor Xa inhibitors as a means of preventing the onset of atherosclerosis and preventing atherosclerotic events.

BACKGROUND

Blood coagulation is a protective mechanism which helps to "seal" defects in the wall of the blood vessels quickly and reliably in the event of an injury. Hemostasis after injury of the blood vessels is effected mainly by the coagulation system in which an enzymatic cascade of complex reactions of plasma proteins is triggered, ultimately resulting in an insoluble fibrin blood clot. Numerous blood coagulation factors are involved in this process.

The coagulation cascade of secondary hemostasis has two initial pathways which lead to fibrin formation. These are the contact activation pathway (also known as the intrinsic pathway), and the tissue factor pathway (also known as the extrinsic pathway), which both lead to the same fundamental reactions that produce fibrin. The pathways are a series of reactions, in which a zymogen (inactive enzyme precursor) of a serine protease and its glycoprotein co-factor are activated to become active components that then catalyze the next reaction in the cascade, ultimately resulting in cross-linked fibrin.

The intrinsic and the extrinsic pathways both lead to a common path in which the zymogen "factor X" is activated to form "factor Xa" (FXa). The activated serine protease FXa cleaves prothrombin to form thrombin. The resulting thrombin, in turn, cleaves fibrinogen to fibrin, a fibrous/gelatinous coagulant. In addition, thrombin is a potent effector of platelet aggregation which likewise contributes significantly to hemostasis.

Thrombin is a key regulatory enzyme in the coagulation cascade. It serves a pluralistic role as both a positive and negative feedback regulator in normal hemostasis. However, in some pathologic conditions, the positive feedback regulation is amplified through catalytic activation of cofactors required for thrombin generation, such as FXa. Thrombin cleaves fibrinogen to fibrin, activates platelets, and converts factor XIII to XIIIa which is the principal enzyme involved in thrombus generation, growth, and stabilization. Accordingly, the location of the prothrombinase complex at the convergence of both the intrinsic and extrinsic coagulation pathways suggests that inhibition of factor Xa, and hence thrombin generation, may be a viable approach to limiting the procoagulant activity of thrombin.

Factor Xa and thrombin are viable targets for anticoagulation therapies, but have also been shown to participate in other biological and pathophysiological processes. Therefore, the properties of oral, direct inhibitors of FXa (e.g. apixaban and rivaroxaban) and thrombin (e.g. dabigatran) have been studied outside the realm of haemostasis and thromboembolism management. See: Henri M. H. Spronk et al., "Pleiotropic effects of factor Xa and thrombin: what to expect from novel anticoagulants," *Cardiovascular Res.* (2014) 101, 344-351. DOI:10.1093/cvr/cvt343, which is herein incorporated by reference in its entirety.

After vascular injury, factor X is activated on the surface of tissue-factor bearing cells such as smooth muscle cells (SMC). See Andreas Böhm et al., "Factor-Xa-induced mitogenesis and migration require sphingosine kinase activity and S1P formation in human vascular smooth muscle cells," *Cardiovascular Res.* (2013) 99, 505-513. DOI:10.1093/cvr/cvt112. Besides its function in blood coagulation, FXa can stimulate vascular SMC proliferation and migration and alter the composition of the extracellular matrix. These events are implicated in the development of atherosclerosis and restenosis after vascular injury. See Andreas Böhm et al.

Direct cellular effects of thrombin and FXa on SMC are mediated by protease-activated receptors (PAR1 to PAR-4), a subgroup of the G-protein-coupled receptors (GPCRs). Thrombin acts through PAR1, PAR3, and PAR4, while FXa activates PAR1 and PAR2. PAR2 does not respond to thrombin. Although both factors signal through PARs, PAR1 induced responses differ according to the nature of the ligand, whereas PAR2 (a receptor for FXa but not for thrombin) is implicated in fibroproliferative disorders. See Henri M. H. Spronk et al. Consequently, unrestrained coagulation activity and/or excessive PAR activation may be involved in a range of conditions, including arthritis, fibrotic lung disease, cancer, and atherosclerosis. See Henri M. H. Spronk et al.

Thus, FXa is believed to trigger acute inflammatory responses via the activation of PAR2, by causing activation of nuclear factor KB (NF- KB) in endothelial cells, which leads to the release of interleukin-6 (IL-6), IL-8, and monocyte chemotactic protein-1 (MCP-1), which contributes to leukocyte recruitment. See Qianxing Zhou et al. "Evaluation of Plaque Stability of Advanced Atherosclerotic Lesions in Apo E-Deficient Mice after Treatment with the Oral Factor Xa Inhibitor Rivaroxaban," Mediators of Inflammation, (2011), Article ID 432080, 9 pages. DOI:10.1155/2011/432080.

The direct cellular effects of FXa are responsible for promoting inflammation, leucocyte transendothelial migration, angiogenesis, and narrowing of blood vessels, which are ultimately the basis of atherosclerotic plaque development. Thrombin activity has also been recognized as playing a role in the development of atherosclerotic plaques. See Henri M. H. Spronk et al.

The cross-talk activation and regulation between coagulation and inflammation processes via PAR activation may be relevant for a number of clinical conditions, including atherosclerosis. See Henri M. H. Spronk et al.

Atherosclerosis is a chronic inflammatory disease, characterized by endothelial dysfunction, local inflammation, leukocyte transmigration, and binding of monocytes to the arterial vessel wall, followed by their translocation and differentiation into macrophages. See R. Loeffen et al., "The impact of blood coagulability on atherosclerosis and cardiovascular disease," *J. of Thromb. and Haemostasis,* (2012) 10: 1207-1216. DOI: 10.1111/j.1538-7836.2012.04782.x The internalization of oxidized lipoproteins by macrophages results in the formation of macrophage foam cells, which induce the secretion of mitogenic and chemoattractant products, facilitating processes such as vascular smooth muscle cell proliferation, migration, and fibrous cap formation, eventually leading to the formation of a mature fatty streak. See R. Loeffen et al. Progression of a fatty streak will result in the development of atheroma, consisting of a core region of foam cells and extracellular lipids, surrounded by a cap of smooth muscle cells and a collagen-rich matrix. If an atherosclerotic plaque ruptures, collagen and tissue factor are exposed, and, through the activation of platelets and the coagulation cascade, atherothrombosis is triggered. Platelets play an important role, as evidenced by the inhibitory potential of platelet inhibitors in atherothrombotic disease, including myocardial infarction. By contrast, the contribution of coagulation proteins to the processes of atherosclerosis and thrombosis remains speculative. See R. Loeffen et al.

Thus, coagulation factors are present in in atherosclerotic lesions. See Loeffen, n. 9, and Julian Icheff Borisoff et al., "The Hemostatic System as a Modulator of Atherosclerosis," *N Engl J Med* 2011;364:1746-60. doi: 10.1056/NEJMra1011670. Tissue factor is a primary physiologic trigger of the coagulation cascade. See Loeffen, n. 9, and Julian Icheff Borisoff et al. Elevated levels of tissue factor are found in atherosclerotic lesions in patients with unstable angina or myocardial infarction, suggesting a role for tissue factor in plaque thrombogenicity. See Loeffen, n. 9, and Julian Icheff Borisoff et al. However, the role is less than clear because reduced vascular expression of tissue factor does not affect atherosclerotic progression in transgenic mice. See Loeffen, n. 9, and Julian Icheff Borisoff et al.

The most significant clinical complication from atherosclerosis is acute occlusion due to thrombus formation, resulting in myocardial infarction or ischemic stroke. The thrombus formation from atherosclerosis is associated with rupture or erosion of unstable atherosclerotic lesions, as post thrombotic content of necrotic cores get exposed to circulating thrombocytes. See Zhou et al., n. 6 supra, at 1-2. Advanced lesions can also grow sufficiently large to block blood flow. See Zhou et al., n. 6 supra, at 1-2. Thus stabilization of atherosclerotic lesions is associated with reduced atherosclerotic events. See Spronk, n. 1 supra, FIG. 5.

There are reports that hemophiliacs appear to have reduced cardiovascular mortality compared to the general population. See Pieter W. Kamhuisan and Hugo ten Cate, "Cardiovascular risk in patients with hemophilia," *Blood*, (2014) 123(9), 1297-1301. DOI: 10.1182/blood-201311-453159. Hemophilia occurs in about 1 in 5000 births. See https://www.hemophilia.org/Bleeding-Disorders/Types-of-Bleeding-Disorders/Hemophilia-A The most common form of hemophilia is hemophilia A, caused by Factor VIII deficiency. Also common is "hemophilia B," caused by Factor IX deficiency. See Joel L. Moake, "Hemophilia," Merck Manual. Studies have suggested that hemophiliacs have the same degree of atherosclerosis burden as the general population, and may have an even higher incidence of hypertension, an important cardiovascular risk factor. See Kamhuisan, n. 19. This may be a consequence of the hypocoagulation effect, which is associated with decreased thrombin generation which inhibits thrombus (blood clot) formation. See Kamhuisan, n. 19. This It is also suggested that hypocoagulation increases atherosclerotic plaque stability, which is associated with diminished atherogenic features of vascular endothelium and reduced plaque burden. See Kamhuisan, n. 19.

Moreover, tissue factor (TF), long known as a key initiator of the coagulation cascade, is implicated in cardiovascular disease risk factors. See Jan Steffel et al. "Tissue Factor in Cardiovascular Diseases," *Circulation* (2006); 113: 722-731. DOI: 10.1161/CIRCULATIONAHA.105.567297. TF may be involved in atherogenesis by eliciting thrombosis, and also by direct actions on vascular remodeling and plaque progression or instability. See Jan Steffel et al. at 726. Thus, inhibitors and antagonists of TF may be effective in treating cardiovascular disease. See Jan Steffel et al. at Abstract and 728.

It has been reported, in mouse models using ApoE$^{-/-}$mice, that rivaroxaban, a leading direct factor Xa inhibitor, stabilized atherosclerotic plaques and attenuated plaque progression. See Tomoya Hara et al., "Rivaroxaban, a novel oral anticoagulant, attenuates atherosclerotic plaque progression and destabilization in ApoE-deficient mice," *Atherosclerosis* (2015); 242(2); 639-646. DOI:10.1016/j.atherosclerosis.2015.03.023. ApoE$^{-/-}$mice are a widely used mouse model for atherosclerosis research because these mice develop atherosclerotic plaques resembling human atherosclerotic plaques. It was found that administration of rivaroxaban did not change plasma levels of FXa or thrombin antithrombin, but mice treated with rivaroxaban were found to have changes associated with attenuation of plaque progression and decreased destabilization of atherosclerotic plaques. See Tomoya Hara et al. at 642. ApoE$^{-/-}$mice treated with rivaroxaban were found to have decreased lipid deposition in plaques. The treated mice also had increased collagen contents in atherosclerotic plaques and decreased expression of matrix metallopeptidase-9 (MMP-9), which is responsible for the degradation of fibrillary collagen, leading to more stable plaques. The treated mice also had reduced accumulation of macrophages in plaques. Since increased lipid deposition, increased macrophage accumulation, and loss of collagen are features of unstable plaques in humans, the administration of rivaroxaban may reduce these factors. See Tomoya Hara et al. at 642-643. Evidence is also available that FXa promotes pro-inflammatory activation of macrophages and endothelial cells. See Tomoya Hara et al. at 643.

Another study of the effect of FXa/FIIa inhibition on experimental aortic aneurysm in apolipoprotein E-deficient (ApoE−/−) mice infused with angiotensin II (AngII)n found that Factor Xa stimulated Smad2/3 phosphorylation and MMP2 expression in aortic vascular smooth muscle cells (VSMC) in vitro. Expression of MMP2 in FXa stimulated VSMC was downregulated in the presence of a PAR-2 but not a PAR-1 inhibitor. These findings suggest that FXa/FIIa inhibition limits aortic aneurysm and atherosclerosis severity due to down-regulation of vascular PAR-2-mediated Smad2/3 signaling and MMP2 expression. See Moran, C. S. et al. "Parenteral administration of factor Xa/IIa inhibitors limits experimental aortic aneurysm and atherosclerosis," Sci. Rep. 7, 43079; doi: 10.1038/srep43079 (2017).

BRIEF SUMMARY

Patients with Factor X deficiency have been noted to be immune, or have a substantial level of immunity, from cardiovascular complications, including development of atherosclerosis. This invention provides reduction of FXa activity by the use of direct or indirect FXa inhibitors that has the effect of preventing the onset of atherosclerosis and stabilizing or shrinking atherosclerotic lesions. In accord with this invention, a direct FXa inhibitor is administered to a patient in a dose sufficient to suppress the activity of FXa by about 25% or more less than normal or by about 50% or more less than normal, or by about 75% of normal, to prevent the formation of atherosclerotic plaques in blood vessels or to treat atherosclerosis, or to stabilize atherosclerotic lesions, or to prevent the occurrence or recurrence of atherosclerotic events.

In an embodiment, a method is provided of preventing atherosclerosis in a patient at risk for atherosclerosis comprising administering an inhibitor of factor Xa. In an embodiment, a method is provided of preventing atherosclerotic events comprising administering an inhibitor of factor Xa. In an embodiment, a method is provided of stabilizing atherosclerotic plaques comprising administering an inhibitor of factor Xa. In an embodiment, a method is provided of treating atherosclerosis in a human suffering from atherosclerosis, comprising administering an inhibitor of factor Xa. In an embodiment, a method is provided of reducing the size and extent of atherosclerotic plaques in a patient suffering from atherosclerosis.

In an embodiment, the inhibitor of factor Xa is a direct or indirect factor Xa inhibitor. In an embodiment, the inhibitor of factor Xa is selected from the group consisting of rivaroxaban, apixaban, betrixaban, edoxaban, and otamixaban.

In an embodiment, the administration of a factor Xa inhibitor causes measured factor Xa activity of about 25% or less than normal. In an embodiment, the administration of a factor Xa inhibitor causes measured factor Xa activity of about 50% or less than normal. In an embodiment, the administration of a factor Xa inhibitor causes measured factor Xa activity of about 75% of normal.

In an embodiment, a direct inhibitor of factor Xa is used for the manufacture of a medicament for the prevention of atherosclerosis in a patient at risk for atherosclerosis. In an embodiment, a direct inhibitor of factor Xa is used in the manufacture of a medicament for the treatment of atherosclerosis in a human suffering from atherosclerosis. In an embodiment, the use of a direct inhibitor of factor Xa is used in the manufacture of a medicament for the prevention of atherosclerotic events.

DESCRIPTION OF THE DRAWINGS

Advantages of embodiments of the present application will be apparent from the following detailed description of the exemplary embodiments thereof, which description should be considered in conjunction with the accompanying drawings in which like numerals indicate like elements, in which:

FIG. 1 is a schematic of the coagulation cascade.

DETAILED DESCRIPTION

Aspects of the invention are disclosed in the following description and related drawings directed to specific embodiments of the application. Alternate embodiments may be devised without departing from the spirit or the scope of the invention. Additionally, well-known elements of exemplary embodiments of the application will not be described in detail or will be omitted so as not to obscure the relevant details of the embodiments. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Referring generally to exemplary FIG. 1 throughout, exemplary embodiments of the invention are based on the observation that patients with factor X deficiency have essentially no cardiovascular disease or atherosclerosis, despite in many cases having other risk factors for atherosclerosis. Persons with naturally low factor X also have low levels of FXa. This can be measured with the anti-FXa test. See Barrett Y, Wang Z, Frost C et al. "Clinical laboratory measurement of direct factor Xa inhibitors: anti-Xa assay is preferable to prothrombin time assay." Thromb Haemost. (2010) 104:1263-1271. DOI: 10.1160/TH10-05-0328, which is incorporated herein by reference in its entirety. Accordingly, in an embodiment of this invention, the administration of a direct FXa inhibitor, which medically induces the same low FXa condition of persons with factor X deficiency, is used to prevent or treat atherosclerosis, and to prevent atherosclerotic events.

About one person per million has inherited Factor X deficiency. There is a strong association between coagulation factor activity level and clinical bleeding severity for Factor X. Recommended trough level of the normal Factor X plasma level to maintain asymptomatic state was increased to 40 percent of normal after publication of the results from the European Network of Rare Bleeding Disorders. See: Palla, R., et al, "Rare bleeding disorders: diagnosis and treatment," Blood, (2015), blood-2014-08-532820, https://doi.org/10.1182/blood-2014-08-532820, the contents of which are hereby incorporated by reference in their entirety. A 2012 clinical trial found no increased prevalence of major bleeding when matched patients were given either the Factor Xa inhibitor apixaban or a placebo. See: G. Agnelli et al, "Apixaban for extended treatment of venous thromboembolism," N Engl J Med. 2013 Feb 21;368 (8):699-708. doi: 10.1056/NEJMoa1207541. Epub 2012 Dec 8, the contents of which are hereby incorporated by reference in their entirety.

In an exemplary embodiment, the administration of an FXa inhibitor to a patient prevents the occurrence or recurrence of atherosclerotic events in a patient. Atherosclerotic events are clinical events such as heart attack (myocardial infarction), stroke (brain ischemia), and ischemic events elsewhere in the body. These are serious medical complications with significant morbidity that are also a major cause of death. Generally, thrombolytic events caused by atherosclerosis may be prevented by embodiments described herein.

Any of several known direct FXa inhibitors, if given in doses that effect sufficient inhibition of FXa, are expected to mimic the atherosclerosis-protective effect of Factor X deficiency. Direct FXa inhibitors are drugs that directly inhibit the activity of FXa specifically and selectively, without requiring a co-factor such as antithrombin III for antithrombotic activity. Direct FXa inhibitors block free and clot-bound FXa and prothrombinase activity. Direct FXa inhibitors have minimal effect on platelet aggregation. Thus, direct FXa inhibitors directly prevent thrombolytic events by inhibiting thrombus formation.

In contrast, an exemplary method is described, in an embodiment of this invention, of preventing the occurrence or recurrence of thrombolytic events caused by atherosclerosis by the administration of a direct inhibitor of FXa. This is a distinct activity as compared to direct inhibition of thrombus formation caused by direct FXa inhibitors. Rather, in this embodiment, the prevention of atherosclerotic events is caused by the stabilization and reduction of atherosclerotic plaques.

A number of direct FXa inhibitors have been approved or are in development. These are described as follows.

Rivaroxaban, which is marketed by Janssen Pharmaceuticals under the trade name XARELTO®. Rivaroxaban is a selective inhibitor of FXa, and was the first direct FXa inhibitor approved in the United States. Rivaroxaban does not require a cofactor (such as Anti-thrombin III) for activity. Rivaroxaban inhibits free FXa and prothrombinase activity. Rivaroxaban has no direct effect on platelet aggregation, but indirectly inhibits platelet aggregation induced by thrombin. By inhibiting FXa, rivaroxaban decreases thrombin generation. The chemical structure is:

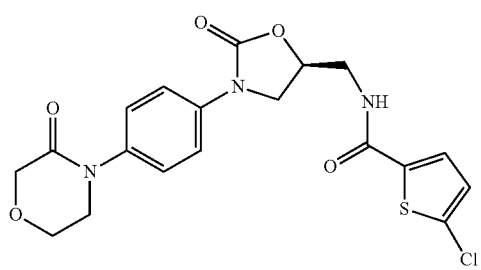

Structure of rivaoxaban

Apixaban, marketed in the United States as "ELIQUIS®" by Bristol-Myers Squibb. Apixaban is a selective inhibitor of FXa that does not require antithrombin III for antithrombotic activity. Apixaban inhibits free and clot-bound FXa, and prothrombinase activity. Apixaban has no direct effect on platelet aggregation, but indirectly inhibits platelet aggregation induced by thrombin. By inhibiting FXa, apixaban decreases thrombin generation and thrombus development. The chemical structure is:

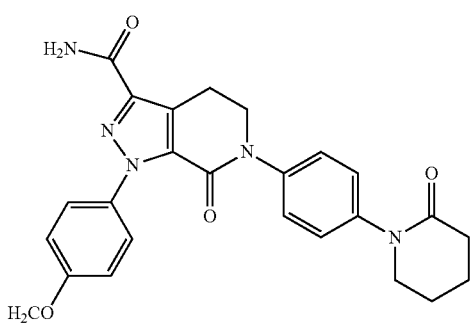

Structure of apixaban

Betrixaban, under development in the United States by Portola Pharmaceuticals, Inc. Betrixaban is a potent, orally active and highly selective direct FXa inhibitor, with low hERG affinity. See Penglie Zhang et al. "Discovery of betrixaban (PRT054021), N-(5-chloropyridin-2-yl-2-(4-(N, N-dimethylcarbamimidoyl)benzamido)-5-methoxybenzamide, a highly potent, selective, and orally efficacious factor Xa inhibitor," Bioorganic & Medicinal Chem. Lett., (2009) 19(8), 2179-2185. DOI: 10.1016/j.bmcl.2009.02.111, which is incorporated by reference herein in its entirety. Betrixaban has undergone several human clinical trials with promising results, and has completed a favorable Phase III clinical trial. See https://www.portola.com/clinical-development/betrixaban-fxa-inhibitor/, which is herein incorporated by reference in its entirety. The structure is:

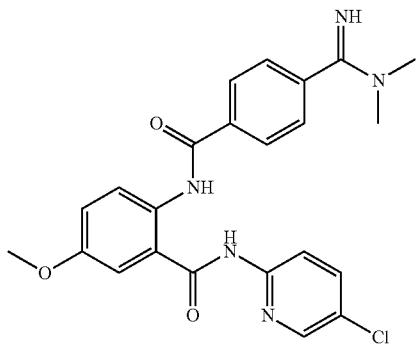

Structure of Betrixaban

Otamixaban. This drug is an is an injectable anticoagulant direct factor Xa inhibitor, that was investigated for the treatment for acute coronary syndrome by Sanofi Aventis, but development was terminated after poor performance in a Phase III clinical trial. The structure is:

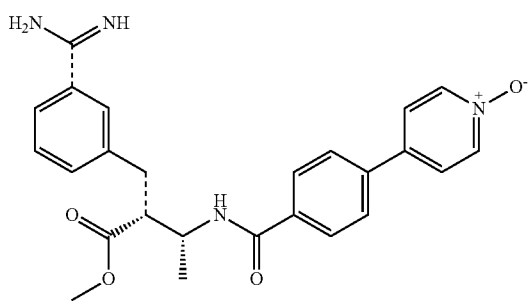

Structure of otamixaban

Edoxaban (DU-176b) is marketed in the United States under the trade name SAVAYSA™ by Daiichi Sankyo. Edoxaban is an oral direct factor Xa inhibitor. It was approved in July 2011 in Japan for prevention of venous thromboembolisms (VTE) following lower-limb orthopedic surgery. It was also approved by the FDA in January 2015 for the prevention of stroke and non-central-nervous-system systemic embolism. The structure is:

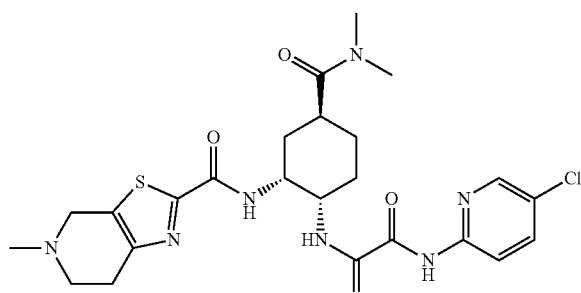

Structure of Edoxaban

This list of direct FXa inhibitors is merely exemplary, however, and additional direct FXa inhibitors may be in development and may have clinical advantages over existing inhibitors. Accordingly, this list is not limiting.

In accord with exemplary embodiments, FXa is a modifiable risk factor in the treatment and prevention of atherosclerosis. Such modifiable risk factors include smoking, diet, diabetes, elevated body weight (high body mass index (BMI)), high blood pressure, and high cholesterol. Each of these factors can be modified by lifestyle changes or drugs, and keeping these factors under control and within medically desirable limits, even if the aid of drugs is required, greatly reduces the risk from atherosclerosis. Likewise, reduction of FXa levels with FXa inhibitors can reduce the risk of medical complications from atherosclerosis and atherosclerotic events.

By the administration of a direct FXa inhibitor that reduces the activity of FXa by about 25% or greater (from normal FXa levels), the development of atherosclerosis will be prevented in patients so treated. In an exemplary embodiment, the activity of FXa is reduced by about 50%. In another exemplary embodiment, the activity of FXa is reduced by about 75%. The reduction of FXa activity by exemplary embodiments described herein is generally limited by the bleeding side effect that can occur if FXa activity falls too low, which inhibits the normal formation of thrombin and blood clotting. Conversely, the dose of an FXa inhibitor should be sufficient to stabilize atherosclerotic plaques or prevent their growth or formation to cause the prevention of atherosclerotic events of this invention. In an exemplary embodiment, a minimum reduction of FXa to achieve a reduction in atherosclerotic events according to this invention is about a 25% reduction of normal FXa levels.

Thus, in the exemplary embodiments, direct FXa inhibitors exert the atherosclerotic preventative effect of the instant invention by the pleiotropic effect of the direct FXa inhibitors on the anticoagulation cascade and PAR-mediated signaling. Inhibitors of FXa inhibit both the conversion of prothrombin to thrombin and FXa-mediated activation of PAR1 and PAR2. See Spronk, n. 1, at 348.

Regarding the PAR effect, the contribution of FXa to atherosclerosis is either directly via binding and inhibition of PAR1 and/or PAR2, which causes mitogenic effects. See Spronk, n. 1, at 346. FXa participation in the atherosclerotic process may be due to orchestration of several signaling pathways in vascular cells, such as endothelial cells and smooth muscle cells, or in immune cells that contribute to atherosclerotic plaque progression. See Spronk, n. 1, at 346. FXa-mediated mitogenic effects affect coronary artery smooth muscle cells (SMCs) via PAR1 in heart- and lung-resident fibroblasts. PAR2 activation may be involved in vascular remodeling and atherosclerosis. These effects are caused by proteolytic cleavage of PAR1 and PAR2 mediated by FXa or thrombin that results in the activation of a canonical G-protein pathway and, consequently, of downstream signaling pathways that trigger multiple transcription-regulated, cell-specific events. The mitogenic effects of FXa induce the expression of chemokines and profibrotic cytokines, including pro-inflammatory cytokine expression (interleukin (IL)-6, IL-8, and monocyte chemoattractant protein (MCP)-1) by fibroblasts, lymphocytes, and endothelial cells in addition to adhesion molecules in monocytes. See Spronk, n. 1, at 346. These mitogenic effects lead to inflammation and the proliferation of atherosclerotic plaques. Thus, without FXa activation of PAR1 and PAR2, in accordance with exemplary embodiments of the invention, this PAR activation and PAR mediated mitogenesis and inflammation will be substantially diminished or will not occur.

The other pleiotropic effect is the mediation of the conversion of prothrombin to thrombin by FXa. Thrombin is also a co-factor in PAR1 activation. Thrombin promotes the expression of adhesion molecules, growth factors, and cytokines in mononuclear leucocytes and endothelial cells. Thrombin also increases the expression of adhesion molecules on leucocytes and their activation, and thrombin-activated platelets can potentiate CD40 ligand-mediated stimulation. Conversely, inflammatory cytokines are known to initiate coagulation by promoting the expression of cellular membrane-bound TF and fibrinogen. The cross-talk activation and regulation between the coagulation and inflammation processes via PAR activation may be relevant in atherosclerosis. See Spronk, n. 1, at 346. Thus, MCP-1 (a cytockine), induced by thrombin, is abnormally expressed in atherosclerotic vessels. See Spronk, n. 1, at 347. Thrombin has been shown to be active in atherosclerotic vessel walls. See A. Allart Stoop et al., "Colocalization of Thrombin, PAI-1, and Vitronectin in the Atherosclerotic Vessel Wall," Arterioscl. Thromb. Vasc. Biol., (2000) 20: 1143-1149. DOI: 10.1161/01.ATV.20.4.1143, the contents of which are hereby incorporated by reference in their entirety. Thrombin inhibition by binding to a recombinant fraction of thrombomodulin impaired PAR1 internalization and reduced the expression of adhesion molecules and MCP-1 in endothelial cells while increasing the permeability of these cells. See Hsi-Ju Wei et al., "Thrombomodulin domains attenuate atherosclerosis by inhibiting thrombin-induced endothelial cell activation," Cardiovasc. Res., (2011) 92 (2) 317-327. DOI: 10.1093/cvr/cvr220, the contents of which are hereby incorporated by reference in their entirety. Also, in ApoE$^{-/-}$ mice, thrombin inhibition reduced the expression of PAR1, adhesion molecules, and infiltrating macrophages, and reduced the development of atherosclerotic plaques. See Julian I. Borissoff et al., "Genetic and Pharmacological Modifications of Thrombin Formation in Apolipoprotein E-deficient Mice Determine Atherosclerosis Severity and Atherothrombosis Onset in a Neutrophil-Dependent Manner," PLoS ONE (2013) 8(2): e55784. DOI: 0.1371/journal.pone.0055784, the contents of which are hereby incorporated by reference in their entirety. This indicates that inhibition of thrombin by direct FXa inhibitors may exhibit the same effects.

Accordingly, in an embodiment, this invention provides the administration of direct FXa inhibitors in an amount sufficient to suppress FXa activity in an amount sufficient to suppress the formation of atherosclerotic plaques. In an embodiment, atherosclerosis is prevented in a patient otherwise at risk for atherosclerosis by the administration of a direct FXa inhibitor in an amount sufficient to suppress inflammatory responses normally attributable to FXa or thrombin. In an embodiment, clinical events caused by atherosclerosis (atherosclerotic events) are prevented by the administration of a direct FXa inhibitor in an amount sufficient to suppress inflammatory responses normally attributable to FXa or thrombin. In an embodiment, atherosclerotic plaques are stabilized by the administration of a direct FXa inhibitor in an amount sufficient to suppress inflammatory responses normally attributable to FXa or thrombin. In an embodiment, the atherosclerotic plaques, also termed lesions, are reduced in size by the administration of a direct FXa inhibitor in an amount sufficient to suppress inflammatory responses normally attributable to FXa or thrombin.

In an embodiment, the direct FXa inhibitor is selected from one of rivaroxaban, apixaban, betrixaban, edoxaban, or otamixaban.

Apixaban can be supplied in about 2.5 mg to about 5.0 mg tablets. Administration is recommended twice per day, in some exemplary embodiments. For example, a typical maintenance dose in moderately healthy adults can be about 5.0 mg twice per day. The major risk from apixaban is bleeding, which affected 1.7% of patients (major bleeding events). See ELIQUIS prescribing information, §6.1, the contents of which are hereby incorporated by reference in their entirety. The clinical trials where this was reported were from an older cohort with at least one major risk factor for stroke. The patients expected to benefit from prophylactic apixaban to prevent the onset of atherosclerosis are expected to be generally younger and healthier, and may have a lower bleeding risk.

Rivaroxaban is supplied in about 10 mg, about 15 mg, and about 20 mg tablets, administered once per day. The risk of a major bleeding event was 4.3% in one reported study, and 1.7% in a second study. See XARELTO prescribing information, §6.1, the contents of which are hereby incorporated by reference in their entirety. The usual dose was about 15 mg to about 20 mg per day. The patients expected to benefit from prophylactic rivaroxaban to prevent the onset of atherosclerosis are expected to be generally younger and healthier than the patients in the rivaroxaban studies, and may have a lower bleeding risk.

Some further exemplary embodiments related to Factor X deficient patients are as follows.

Patient A is a 66 year old male having genetic Factor X deficiency, 36% of normal as measured by anti-Xa assay. His body mass index is 31, and has been over 30 for many years. HDL and LDL ratios are in the moderate risk category (lipid panel score, 5.2, max recommended score is 4.8). Blood pressure is 110/70. Coronary calcium score is 0. See Keith Loria, "Knowing the Score: Cardiologists Are Taking Advantage of Coronary Artery Calcium Scoring's Benefits," Radiology Today, (2004) 15(10) 20 http://www.radiology-today.net/archive/rt1014p20.shtml), the contents of which are hereby incorporated by reference in their entirety. The calcium score is a measure of subclinical coronary atherosclerosis obtained with a noncontrast CT scan of the heart. It is considered one of the best available tests beyond the usual risk factors to refine cardiac risk assessment.

Thus, based on blood pressure and coronary calcium, no sign of atherosclerosis is apparent, despite long term unfavorable lipid panel scores, moderate obesity, and age risk factors.

In a second example, patient B is a 70-year old male with a genetic Factor X deficiency, with Factor X at 53% of normal as measured by anti-Xa assay. He has no had no atherosclerotic events and a coronary calcium score of 0.

The foregoing description and accompanying figures illustrate the principles, preferred embodiments and modes of operation of the application. However, the invention should not be construed as being limited to the particular embodiments discussed above. Additional variations of the embodiments discussed above will be appreciated by those skilled in the art (for example, features associated with certain configurations of the application may instead be associated with any other configurations of the application, as desired).

Therefore, the above-described embodiments should be regarded as illustrative rather than restrictive. Accordingly, it should be appreciated that variations to those embodiments can be made by those skilled in the art without departing from the scope of the invention as defined by the following claims.

The invention claimed is:

1. A method of reducing the likelihood of developing atherosclerosis in a human, comprising:
   measuring factor Xa activity in a patient, and
   administering an inhibitor of factor Xa in an amount effective to reduce activity of factor Xa by 25% or more in a patient having a measured normal factor Xa activity,
   wherein the patient has high cholesterol, and
   wherein the patient has not been diagnosed with atherosclerosis or atherosclerotic plaque.

2. The method of claim 1, wherein the inhibitor of factor Xa is selected from the group consisting of rivaroxaban, apixaban, betrixaban, edoxaban, and otamixaban.

3. The method of claim 2, wherein the inhibitor of factor Xa is rivaroxaban administered in 10 mg to 20 mg tablets.

4. The method of claim 2, wherein the inhibitor of factor Xa is rivaroxaban administered once per day.

5. The method of claim 1, wherein the inhibitor of factor Xa is apixaban administered in 2.5 mg to 5.0 mg tablets.

6. The method of claim 5, wherein the apixaban is administered once per day.

7. The method of claim 2, wherein the inhibitor of factor Xa is betrixaban, or edoxaban.

8. The method of claim 2, wherein the inhibitor of factor Xa is otamixaban.

9. The method of claim 1, wherein the administration of the factor Xa inhibitor causes a decrease in measured factor Xa activity of about 50% or more.

10. The method of claim 1, wherein the administration of the factor Xa inhibitor causes a decrease in measured factor Xa activity of about 75%.

11. The method of claim 1, wherein the inhibitor of factor Xa is administered in an amount sufficient to suppress inflammatory responses attributable to factor Xa or thrombin.

12. The method of claim 1, wherein administering an inhibitor of factor Xa to the human inhibits the progression of coronary calcium as determined by coronary artery calcium scoring.

13. The method of claim 1, wherein the factor Xa inhibitor is administered in an amount sufficient to suppress the formation of atherosclerotic plaques.

* * * * *